United States Patent
Caldarise et al.

[11] Patent Number: 6,008,431
[45] Date of Patent: Dec. 28, 1999

[54] BONE PROSTHESIS WITH PROTECTED COATING FOR PENETRATING BONE INTERGROWTH

[75] Inventors: Salvatore Caldarise, Hanson; John W. Besemer, Sudbury, both of Mass.; Allan Ritchie, New Milton; Frank R. Foley, Byfleet, both of United Kingdom

[73] Assignee: Johnson & Johnson Professional, Inc., Raynham, Mass.

[21] Appl. No.: 08/713,103

[22] Filed: Sep. 16, 1996

Related U.S. Application Data

[63] Continuation of application No. 08/521,111, Aug. 29, 1995, abandoned.

[51] Int. Cl.$^6$ ......................................................... A61F 2/28
[52] U.S. Cl. ............................... 623/16; 623/11; 623/18; 623/22; 623/23
[58] Field of Search ................. 623/11, 16–23; 606/60, 69–71, 76–77

[56] References Cited

U.S. PATENT DOCUMENTS

| | | | |
|---|---|---|---|
| 4,179,485 | 12/1979 | Tritten | 264/44 |
| 4,722,870 | 2/1988 | White | 623/16 |
| 4,795,472 | 1/1989 | Crowninshield et al. | 623/23 |
| 4,813,959 | 3/1989 | Cremascoli | 623/23 |
| 4,865,603 | 9/1989 | Noiles | 623/16 |
| 4,871,578 | 10/1989 | Adam et al. | 623/16 |
| 4,878,914 | 11/1989 | Miwa et al. | 623/18 |
| 4,944,759 | 7/1990 | Mallory et al. | 623/18 |
| 5,007,931 | 4/1991 | Smith | 623/23 |
| 5,042,560 | 8/1991 | Ahlers | 164/34 |
| 5,108,435 | 4/1992 | Gustavson et al. | 623/16 |
| 5,128,146 | 7/1992 | Hirayama et al. | 623/16 |
| 5,204,055 | 4/1993 | Sachs et al. | 419/2 |
| 5,258,098 | 11/1993 | Wagner et al. | 156/645 |
| 5,344,457 | 9/1994 | Pilliar et al. | 623/16 |
| 5,507,815 | 4/1996 | Wagner et al. | 623/16 |
| 5,507,833 | 4/1996 | Bohn | 623/16 |
| 5,514,184 | 5/1996 | Doi et al. | 623/22 |
| 5,658,334 | 8/1997 | Caldarise et al. | 623/16 |
| 5,665,118 | 9/1997 | Lasalle et al. | 623/16 |

FOREIGN PATENT DOCUMENTS

| | | |
|---|---|---|
| 0399163 | 11/1990 | European Pat. Off. . |
| 0668062 | 8/1995 | European Pat. Off. . |
| 4211343 | 10/1993 | Germany . |
| 7-2172 | 1/1995 | Japan . |
| 8602824 | 5/1986 | WIPO . |
| 9221302 | 12/1992 | WIPO . |

*Primary Examiner*—Mickey Yu
*Assistant Examiner*—Francis K. Cuddihy
*Attorney, Agent, or Firm*—Nutter, McClennen & Fish, LLP

[57] ABSTRACT

A bone prosthesis has a growth enhancement coating recessed in and protected by its surface topography. The topographic features define gaps under a few millimeters which are readily spanned by new bone growth, while the features protect the coating from abrasion or physical damage. The topographic features substantially surround the coated regions, and prevent migration of flakes spalled during implantation or microparticles shed by the coating as it is resorbed or incorporated in new bone over time. In a preferred embodiment, edge features cast in the surface of a metal prosthesis include dovetail, undercut or skewed faces which firmly interlock with newly-growing bone to form a strong and shear-free, substantially rigid attachment. The prosthesis may be cast in a mold having a complex surface interlock texture, and these molds may be mass produced by an iterative three-dimensional printing technique to build each mold up in layers in the form of a suitable casting negative. The prosthesis is then cast of molten metal in the mold, and the mold material is broken away and cleaned off, e.g., by an etch. A growth enhancer such as hydroxyapatite (HA) is plasma-sprayed to selectively deposit on and completely cover the floors of the recesses formed in the casting. Preferably, the upper surfaces about the recesses are polished, and the recess walls are overhung so they are masked from the coating process, causing the HA coating to adhere only in the protected floor regions. The HA floors are at the bottom of pits or macropores, at a depth of under three millimeters, and preferably one-half to two millimeters, so that new bone growth spans the gaps and penetrates into the prosthesis over an extended surface textured region.

8 Claims, 2 Drawing Sheets

BONE PROSTHESIS WITH PROTECTED COATING FOR PENETRATING BONE INTERGROWTH

This application is a continuation U.S. application Ser. No. 08/521,111, filed Aug. 29, 1995; now abandoned.

BACKGROUND OF INVENTION

The present invention relates to implantable bone prostheses, and more particularly to bone prostheses which are structural in the sense that they are formed of a strong material which is attached to a bone in a way to replace or reinforce all or a portion of the natural bone. Examples of such prostheses include bone plates which are fastened to the bone at a fracture site to connect separated pieces and provide a structural link across a break or crack. Such bone prostheses also include entire joints or articulations or portions thereof, such as are customarily employed to replace or rebuild weakened, diseased or damaged hip joints, knee joints or the like.

In general, it has been found desirable that the prosthesis become incorporated in the existing bone, or at least that new bone growth attach to surfaces of the prosthesis to form a strong junction therewith. Historically, early prostheses sought only a certain level of biocompatibility or nontoxicity for the material employed in the body or outer surface of structural elements forming the prosthesis. This approach essentially treated prosthetic patches as though they were braces or struts used in building construction, and relied extensively on material strength and the fitting or the contour of the article to replace corresponding bone strength. Subsequently, it was learned that bone adheres better to textured surfaces and that particular shapes and sizes of the surface texture or relief on a prosthetic device enhance the regrowth of bone in and around the surface, and increase the strength of the junction so formed. Particular material such as calcined and sintered preparations of coral or mineral-like materials, such as calcium phosphate-hereafter referred to simply as hydroxyapatite (HA)—were found to especially enhance new bone growth and promote incorporation into active bone processes.

Taking for example, a simple prosthetic device such as a replacement stem of a hip joint, these insights as to bone growth enhancement have been applied in several ways, as follows. Such an assembly normally includes a ball, and a stem to which the ball is attached, wherein the stem is tapered, and possibly splined or otherwise shaped to fit within the femur and to rigidly anchor the ball and stem assembly to this major leg bone. The ball itself is generally a polished metal or metal/ceramic article, which may be permanently or removably affixed to the stem portion by a very strong and precisely machined or molded fitting, such as a tapered bore and post. The stem, on the other hand, is typically substantially all metal, such as a titanium or a cobalt chrome alloy, and is intended to bear the load and bending stresses transmitted between stem and bone along the upper leg. While historically femoral stems were initially simply cemented in position with an acrylic or similar cement, subsequent knowledge of bone growth has lead to the development of such stems having textured regions configured for promoting bone growth and enhanced gripping strength with the newly-grown bone. There has been a concomitant reduction and even elimination of the use of cement for initially attaching the stem to the bone at this site.

A number of ways have evolved for creating the aforementioned surface textures, including plasma spraying of metal droplets, baking-on or welding of thin wires or grains onto regions of the surface, and more recently, the direct casting of the article with regions of surface texture formed by a pattern in the casting mold. In the latter approach, several difficulties were initially presented. First, a casting procedure necessarily involves forming a suitable mold and, subsequent to casting of the metal article, removing the mold. The existence of surface texture on the mold and the cast part generally increases the difficulty of separating the two parts. Second, often desirable textures quite simply cannot be separated without breaking the mold. This feature has also presented difficulties for example in attempts to mass produce appropriate molds by conventional processes such as slip casting the mold body over a wax perform.

Problems of this type can be largely overcome by initially making the molds in an automated manner using techniques such as three dimensional printing, which are described in greater detail in commonly assigned U.S. patent applications Ser. No. 08/198,874 and the file wrapper continuation of that application filed on Jun. 6, 1995, as well as the techniques described in U.S. patent application Ser. No. 08/198,607 filed Feb. 18, 1994, as well as in U.S. Pat. No. 5,204,055 of Sachs et al., the disclosures of all of which are hereby incorporated herein by reference. Those applications taken together describe techniques for three-dimensional printing or building-up and curing of a form or a mold having an arbitrary bounding surface, so that the article cast therein may be formed with complex or arbitrarily-designed surface protrusions or indentations, including protruding walls of an undercut or overhanging type which would normally be not manufacturable in multiple copies, or which would present great difficulty of proper filling, finishing, or separation from the mold if so manufactured. It also allows the computerized storage and generation of shapes, and the precise modification or scaling of dimensions and contours to allow one to quickly identify and subsequently define shapes suitable for optimal bone growth and attachment, and to manufacture such textured prosthesis in multiple sizes.

So far as relevant to present application, mold and prosthesis forming techniques of the foregoing patent applications are assumed known and their teachings are incorporated by reference herein without further discussion. They allow one to cast a prosthesis with a desired shape of growth-compatible and grip-enhancing surface relief.

In addition to surface texture, various prior art techniques of forming a prosthesis use a bone growth material such as hydroxyapatite, either in the structural body or in regions of the surface of the prosthesis. One such technique has been to form a porous body of hydroxyapatite (HA), which is then filled by casting a metal for reinforcement into the porous body. Another approach is to apply the hydroxyapatite as a surface coating to an already-cast article. Such a coating may be applied, for example, by a plasma spray deposition process in order to firmly adhere the HA material to the surface of an already-cast article. Other techniques of applying an HA coating include painting-on a slurry of hydroxyapatite and baking it at a sufficiently high temperature.

However, the approach of applying such a coating to enhance bone growth and attachment at the surface of a prosthesis has generally fallen into disfavor because both the process of initial handling and implantation, and the resorbability and disintegration in vivo of the hydroxyapatite, result in shedding of flakes and microparticles, and these shed particles can cause adverse bodily reactions, such as lysis and cell reactions, or can become trapped or embedded as abrasive bodies in components in the joint space.

Accordingly, it would desirable to provide a bone prosthesis with enhanced bone growth properties but without the structural disadvantages of prior growth enhancement constructions.

SUMMARY OF INVENTION

These and other desirable features are achieved in accordance with the present invention by an implantable bone prosthesis having a body which attaches to living bone to replace or repair a portion of the bone, and in which the body includes a bonding surface that contacts and attaches to the bone. The bonding surface is formed with bas relief features extending outwardly from a metal casting to define outermost contact or positioning surfaces, and a plurality of recesses extending inwardly of the features to form shallow-bottom pits. The bottoms of these pits are coated with a growth enhancer. The walls of the bas relief features shield or contain the bottom coating from stress and prevent flaking off, and preferably also have an edge trapping orientation such as an overhang which retains the newly-growing bone and prevents lifting-off of the bone, or migration of released coating fragments out of the pits, as the bone heals.

In a preferred embodiment, the features define an enclosed floor protected by dovetail walls that present a gap on the order of one or two millimeters between the coated floor and the outer bone contact surface. These gaps after implantation spontaneously fill with new bone growth. The dovetail wall may define line of sight pattern-defining masks that allow the floors to be entirely coated with the hydroxyapatite material by a spray-like process such as plasma spray deposition. The walls also define structural engagement members as well as physical shields for the growth enhancer coating. In the preferred embodiment, the outermost surface or top of the bas relief is also polished to a shiny smoothness that prevents attachment of the HA coating, so that the body of the prosthesis may be coated in a bulk process atmosphere while nonetheless selectively covering only the pit floors. A mold body for directly casting the prosthesis with its bas relief surface and recesses, may be formed by a three dimensional printing process which builds the mold up layer by layer using a computer to control a patterning head. The head is actuated to spray or treat a loose powder or fluid, and selectively harden a pattern of pixels in each successive layer, thus iteratively building-up the desired mold pattern.

BRIEF DESCRIPTION OF THE DRAWINGS

These and other features of the invention will be understood from the description herein, taken together with the claims and general training and skills available in the art, and together with the illustrations of selected embodiments and details thereof, wherein

DETAILED DESCRIPTION

Figure 1:
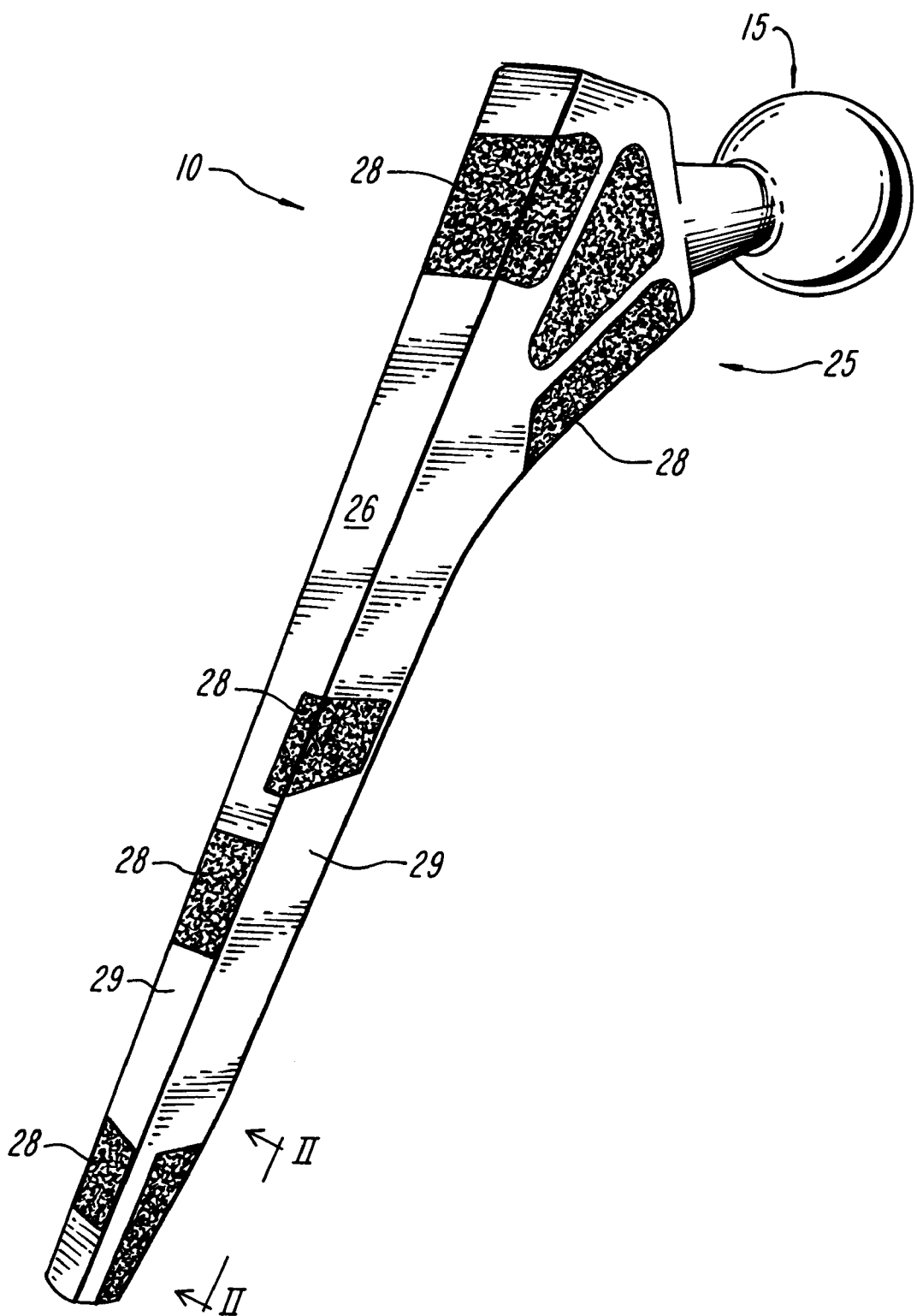
FIG. 1 shows a bone prosthesis in accordance with present invention.

FIG. 1 shows a bone prosthesis 10 in accordance with the present invention illustrated solely by way of example as a hip ball 15 with mounting stem 25. These two components, as is well known, are assembled during surgical installation or prior thereto into a single unit 10. The ball 15 forms a load bearing wear surface that movably bears against an acetabular shell or cup of corresponding size, while stem 25 is fitted into a corresponding bore that is drilled and broached in the patient's femur so that the lower portion 26, comprising a substantial part of the exposed surface of the stem 25, wedges securely into the femur and is eventually anchored therein by new bone growth. Roughened surface-textured regions 28 are provided in the lower stem surface 26 to enhance the formation of high-shear strength bone intergrowth. Smooth regions 29 are also shown in the lower stem. These regions, if included, extend outwardly of the textured regions, so they will contact the surrounding bone. They may wedge or otherwise be secured to provide a reasonably strong degree of initial fixation, while the textured regions are intended to eventually provide a higher strength engagement, after a tinge, with newly-grown bone, to better resist the impacts and stresses encountered in normal use. In overall contour and appearance, the prosthesis 10 is substantially similar to prostheses presently marketed, with the exception that the textured regions 28 of the present invention have the detailed construction described further below, and may be more numerous or distributed over a greater area than in a conventional stem.

Figure 2:
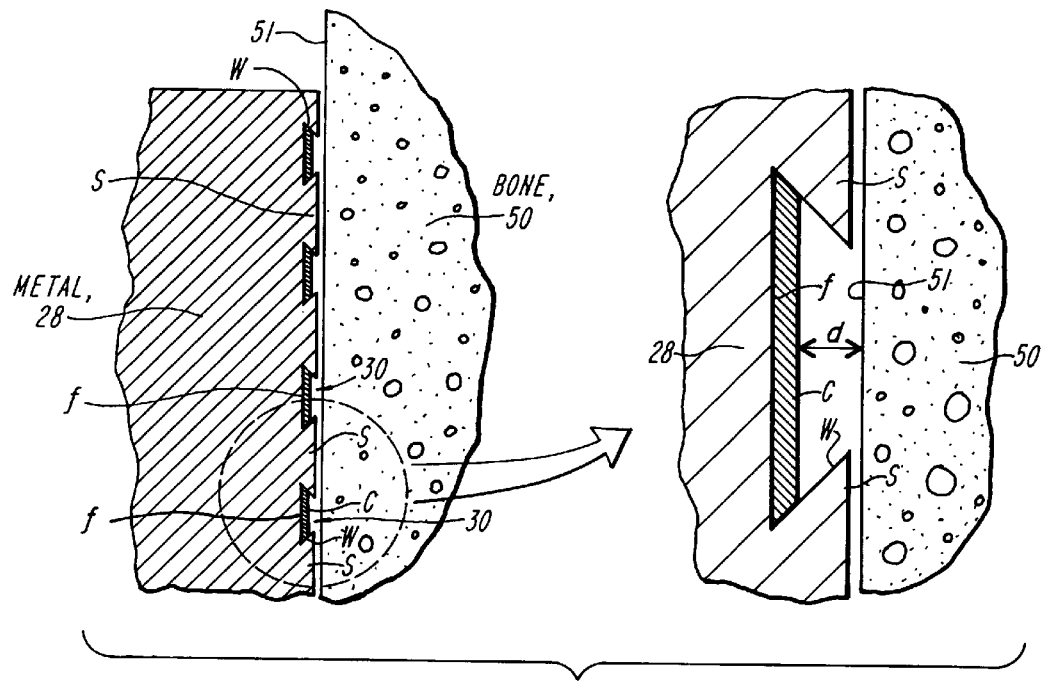
FIG. 2 shows a detail of a representative embodiment thereof.

FIG. 2 shows a section through the lower stem 26 of the prosthesis 10 taken normal to the surface thereof in a textured region 28. The region 28 is characterized by recesses 30 which are set below the upper surface s, and which each have a floor f and are bounded by walls w. The recesses 30 may take many possible forms, e.g., round crater-like pits, long trench-like grooves, or small discrete one-dimensional patterns such as an L-, Z-, or W-shaped, or zigzagged or check-shaped recesses, or two-dimensional arrays of such features, such as a checker board or hound's tooth pattern. Whatever their overall shape or distribution, at the bottom of each recess, a floor f is covered by a coating c of a bone growth enhancer, such as hydroxyapatite (HA) or other similar or bone-like growth and compatibility enhancer. There is no coating c on the upper surfaces s. As with a conventional prosthesis, it is envisaged that the stem 25 is provided in a range of fixed sizes, and installation is effected by drilling and broaching an intramedullary bore in the femur to provide a cavity precisely fitted to the stem's surface envelope. For conceptual clarity, the view of FIG. 2 shows the stem 25 inserted in such a manner, with the inner surface 51 of a bone 50 in contact therewith. In the illustrated preferred embodiment, the walls w are undercut. That is, they overhang the recesses so that these walls are shielded, umbrella-like, from the outside by the material above them. This allows the coating to be applied to the floors by a spray process without depositing on the walls. The walls w thus remain bare metal and form rigid well-defined sides about each recess.

The upper surface viewed along the normal to the prosthesis surface defines a contact surface for alignment with and contacting a bone surface 51, the inner wall of the femur 50, thus placing the recessed floors f at a fixed distance from the bone defined by the surface-to-floor spacing depth d. This depth d is below three millimeters, generally between one-half and three millimeters, and most preferably between about three quarters and one and one-half millimeters, and it may be different for different recesses. By way of example, the recesses may consist of ten to fifty or more small round or square pits, one tenth to several millimeters, and preferably above one-half millimeter, across, distributed over a region of several square centimeters of textured surface. The floor depth may be one-half millimeter in some recesses, one millimeter in others, and one and a half or two millimeters in others. In general, the depth d is selected small enough so that natural bone growth processes will bridge the gap to the floor f with buttons or ridges of newly grown bone that extend into the recesses and form structurally strong extensions of the existing bone. The gap may be set even smaller than a millimeter in some or all of the recesses to assure that a sufficient amount of bone growth and recess-filling occurs early in the post-implantation period to anchor the prosthesis. However, as described further below, the recesses are preferably deeper than about one millimeter to enhance lateral engagement of the new growth. Furthermore, as illustrated, each of the surfaces s may be crowned, i.e., may be slightly convex. Such convexity reduces the possibility of gouging the bone during insertion, increases the distribution of initial points of bone contact over the surface of the stem 25, and provides a localized stress-loading at each contact point which may better promote localized bone regeneration.

At each recess, the walls w and protruding upper surface s shield the coating c from chipping or abrasive contact both during handling and after implantation. Furthermore, as best seen in FIG. 2, the walls preferably surround the recess, so that once the prosthesis is installed in contact with a bone surface, the recesses are bounded or contained by the surrounding wall, and any spalling or chipping during implantation or erosion of the coating on the floor over time remains sealed within the recess, contained between the prosthesis and the opposing bone. The walls also protect the HA coating against shear. This protection is two-fold. Initially each of the recesses amounts to a relatively small-diameter surface "pore" in which the side walls w are closely spaced and provide lateral support for the coating c on the floors of the pores, so that shear forces can not build up over such large regions as to cause cracks to develop in the coating. Secondly, as new bone growth develops, the new growth protrusions from bone wall 51 are engaged about their sides by the prosthesis walls w. Thus, these bone protrusions, which are the only material that contacts the floors, become physically constrained so that they cannot move laterally or apply destructive shear forces to the weak HA coating.

FIG. 2, a section normal to the overall surface contour of the prosthesis, shows walls w which are oblique, so that they overhang the floors of the recesses. When new bone protrusions grow into the recesses these walls engage the new growth along edges and exert a component of force normal to the surface to prevent lift-off of the bone from the prosthesis, in a manner structurally similar to a dovetail joint. The recesses themselves may be elongated recesses, continuous patterns or small symmetric recesses such as round or square holes. For purposes of bone fixation, the critical dimensions are the overall cross-diameter, which should be on the order of a centimeter or less to assure adequate protection of the HA floor, and preferably be one-half to two millimeters for optimal bone gripping; and the depth, which must define a sufficiently small gap for new bone to bridge the gap and fill the recess.

Within these general constraints, the invention may be practiced with surface recess features having a wide variety of shapes. For example, surface features which define an interconnected surface macroporosity as described in the aforesaid U.S. patent application Ser. No. 08/198,874 may be modified in layout to assure that the floor areas are coated with bone growth material and are shielded from stress by the surrounding high relief areas. This may be accomplished, for example, by assuring that protective walls $w_1, W_2 \ldots W_n$ of the stiff metal casting i. extend along at least two distinct directions to anchor newly-grown bone against local twisting (shear);
  ii. are located within a short distance of each other, so that strains do not build up to a magnitude that would cause dislocation or cracking of the coating; and optimally
  iii. together the walls more or less surround or fence-in the coated floor region so that coating material cannot escape from the growth junction region.

As noted above, the prosthesis stem assembly itself is a metal stem, formed as a single casting to which the ball 15 is subsequently attached. The provision of the protective recesses in textured regions 28 is preferably accomplished by patterning the casting mold to define such features, as described in the aforesaid patent and patent applications, although in simpler cases it may also be formed by post-casting machine operation such as dovetail routing. The coating is preferably applied by a plasma spray coating process, and any material on the crowns s may be readily removed by brushing.

Accordingly to this method, the rough-cast prosthesis is first polished so that the surfaces s are smooth, while the floors of the recesses remain rough. The HA floor coating is then applied by a directional spray or electrostatically-or plasma-assisted spray deposition process. The coating does not adhere to the surface s, and is selectively deposited to a controlled depth in the recesses. Slight buffing or a brushing operation then complete the process without generating any significant debris. Thus, despite the complexity and surface detail of the multi-material textured surface construction, the assembly is fabricated by bulk casting, machining, coating and finish operations.

Figure 3:
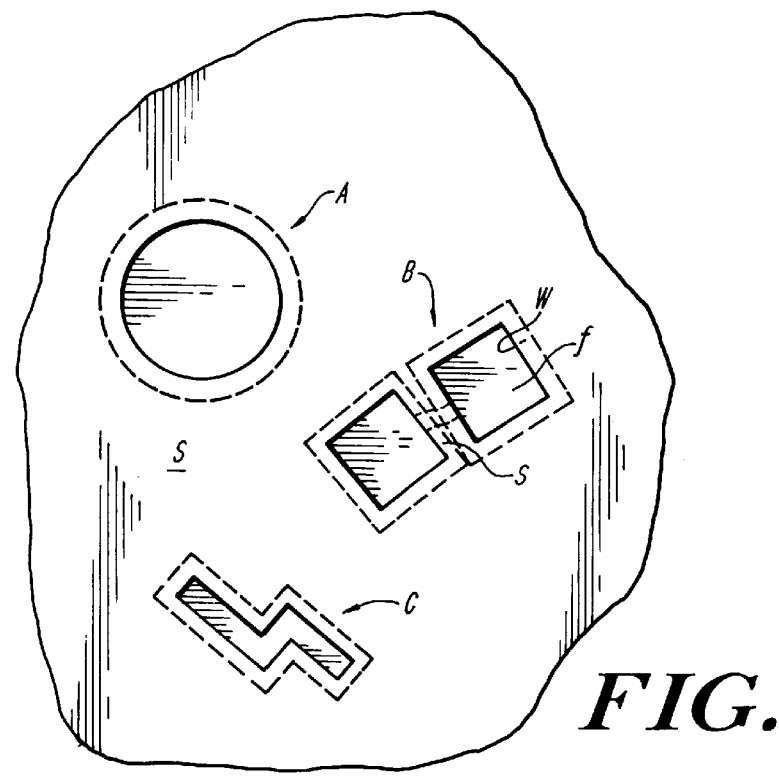
FIG. 3 shows another embodiment of the invention.

FIG. 3 shows a perspective view of several different possible recess pattern regions A, B, C, one or more of which may be replicated in multiple adjacent copies to fill an extended surface area of the cast prosthesis for enhancing bone attachment. In general, the pore pattern may have polished upper surface regions s which have no HA coating, and may have rougher-textured floor regions f on which the coating is adhered and to which the new bone growth will attach. Since the walls w overhang each recess, the total areas of the surface regions s and floor regions f will in general be slightly larger than the overall surface area of the porous region. Furthermore, the total area of the floor regions f is a substantial fraction, preferably over twenty percent and as much as ninety percent, of the relevant surface area. On the other hand, the raised portions should in general not be so small, or individually be so thin as to create destructive pressures or dig into the bone surface 51 against which they bear. The raised surfaces s may for example have a minimal cross dimension of at least one half, and up to several millimeters. In the preferred embodiment, the size of the recessed floor is comparable to the size of the raised plateau s between recesses.

The invention being thus disclosed, other variations and modifications, as well as adaptations to known prosthetic devices will occur to those skilled in the art, and all such variations, modifications and adaptations are within the spirit and scope of the invention, as defined in the claims appended hereto.

What is claimed is:

1. An implantable bone prosthesis comprising:
   a structural body having a coating of bone growth enhancer applied in a plurality of recesses thereon, whereon the coating is protected and enclosed by opposing substantially planar undercut walls which surround the recesses, the undercut walls defining at one end an opening and at an opposite end a substantially planar floor upon which is adhered the coating, wherein the opening has a first diameter and the floor has a second diameter which is greater than the first diameter, the undercut walls further defining dovetail-like projections between adjacent recesses.

2. The prosthesis of claim 1, wherein the planar walls intersect the planar floor at an acute angle.

3. The prosthesis of claim 1, wherein the recesses are all the same shape.

4. The prosthesis of claim 3, wherein the recesses are all the same size.

5. The prosthesis of claim 1, wherein the coating is uniformly distributed on the floor.

6. The prosthesis of claim 1, wherein the openings are co-planar.

7. The prosthesis of claim 1, wherein the depth of the recesses is uniform.

8. The prosthesis of claim 1, wherein the bone growth enhancer coating is a hydroxyapatite coating and the planar floor has a roughened texture.

\* \* \* \* \*

UNITED STATES PATENT AND TRADEMARK OFFICE
CERTIFICATE OF CORRECTION

PATENT NO. : 6,008,431
DATED : December 28, 1999
INVENTOR(S) : Salvatore Caldarise et al.

It is certified that error appears in the above-indentified patent and that said Letters Patent is hereby corrected as shown below:

On the Cover Page:

item, [75] Inventors, the following inventor should be added:

Debra J. Treacy, Middleborough, Massachusetts

Signed and Sealed this

Twenty-sixth Day of September, 2000

Attest:

Q. TODD DICKINSON

*Attesting Officer*    *Director of Patents and Trademarks*